(12) United States Patent
Knappe

(10) Patent No.: US 8,182,797 B2
(45) Date of Patent: May 22, 2012

(54) STYLING AGENT

(75) Inventor: Thorsten Knappe, Schenefeld (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 68 days.

(21) Appl. No.: 12/793,779

(22) Filed: Jun. 4, 2010

(65) Prior Publication Data

US 2010/0239623 A1    Sep. 23, 2010

Related U.S. Application Data

(63) Continuation of application No. PCT/EP2008/065122, filed on Nov. 7, 2008.

(30) Foreign Application Priority Data

Dec. 5, 2007 (DE) .......................... 10 2007 058 921

(51) Int. Cl.
*A61Q 5/06* (2006.01)

(52) U.S. Cl. ................................. 424/70.122; 424/70.16

(58) Field of Classification Search .................. None
See application file for complete search history.

(56) References Cited

U.S. PATENT DOCUMENTS

| 5,773,595 A | 6/1998 | Weuthen et al. |
| 6,235,913 B1 | 5/2001 | Raths et al. |
| 2003/0147834 A1 | 8/2003 | Rollat et al. |

FOREIGN PATENT DOCUMENTS

| AU | 730455 B2 | 3/2001 |
| DE | 19756454 C1 | 6/1999 |
| WO | 2007118807 A2 | 10/2007 |

OTHER PUBLICATIONS

Lee, Haeshin et al. A Reversible wet/dry adhesive inspired by mussels and geckos. Nature, vol. 448, 2007, pp. 338-341.pdf.

*Primary Examiner* — Jyothsna Venkat
(74) *Attorney, Agent, or Firm* — David P. LeCroy

(57) ABSTRACT

Cosmetic agent for temporarily deforming keratin fibers, comprising a polysilicic acid in a cosmetically acceptable carrier, wherein the polysilicic acid is coated with at least one copolymer A formed from at least one monomer A1 according to Formula (A1)

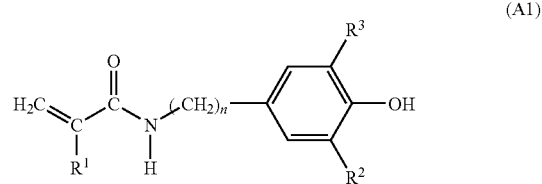

(A1)

wherein $R^1$ is H or $CH_3$, $R^2$ and $R^3$ each independently of each other mean H, OH, $C_{1-10}$-Alkyl or $C_{1-10}$-Alkoxy, under the provision that at least one of the radicals $R^2$ or $R^3$ is OH, and n is a whole number from 0 to 20, and at least one monomer A2 according to Formula (A2)

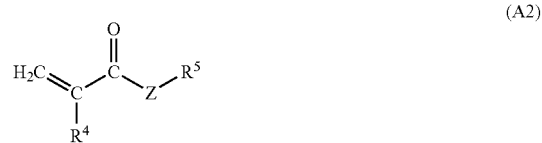

(A2)

wherein $R^4$ is H or $CH_3$, Z is O or NH, and $R^5$ is $C_{1-30}$-alkyl or $C_{1-30}$-alkylene-$C_{1-30}$-alkylether group, use of the agent for temporarily deforming keratin fibers, and method of deforming hair using such agent.

14 Claims, No Drawings

STYLING AGENT

CROSS REFERENCE TO RELATED APPLICATIONS

The present application is a continuation of International Application No. PCT/EP2008/065122 filed 7 Nov. 2008, which claims priority to German Patent Application No. 10 2007 058 921.4 filed 5 Dec. 2007.

The present invention relates to cosmetic compositions comprising a polysilicic acid coated with a certain copolymer A for temporarily shaping keratin fibers, to the use of said compositions for temporarily shaping keratin fibers and to methods for hair styling employing said compositions.

Keratin fibers are in principle understood to include all animal hair (e.g., wool, horsehair, angora hair, furs, feathers) and products or fabrics produced from them. However, keratin fibers preferably concern human hair.

Today, a suitably looking hairstyle is generally regarded as an essential part of a well groomed appearance. Based on actual fashion trends, time and again hairstyles are considered chic, which, for many types of hair, can only be formed or sustained over a longer period by use of certain consolidating materials or by targeted modifications of the hair structure. Thus, hair treatments which provide a permanent or temporary hairstyling play an important role.

A gentle method for shaping keratin-containing fibers is temporary hair styling, achieved by conventional hair sprays, hair waxes, hair gels, hairdryer waving, etc.

Suitable compositions for temporary hairstyling usually comprise synthetic polymers as the styling component. Preparations comprising a dissolved or dispersed polymer can be applied onto hair by propellants or a pumping mechanism. However, other compositions such as hair gels and hair waxes are not generally applied directly on the hair, but rather dispersed with a comb or by hand.

An important property of a composition for temporary styling of keratin fibers (hereinafter referred to as styling compositions) consists in giving the treated fibers the strongest possible hold in the created shape. If the keratin fibers concern human hair, then one also speaks of a strong hairstyle hold. Moreover, the user of a styling agent increasingly expects the created hairstyle to remain shapeable without loosing the hold due to reshaping. In this context, the term, "remodelability" of a hairstyle is used. Also, moisture resistance often plays a role. The created hairstyle should be resistant to high levels of atmospheric humidity and to perspiration.

Available styling agents that lend a good hold to the hairstyle are generally based on film-forming and/or setting polymers. The degree of hold can be adjusted by an appropriate choice of the type and/or concentration of the film forming and/or setting polymers. The polymers form a film on the treated fiber and link individual fibers to one another such that the fibers are fixed in a predetermined position. Should a fixed hairstyle be subjected to mechanical stress then the polymer film is easily broken, linkage sites are irreversibly disconnected and the hold of the fibers is lost. Because deformation of the hairstyle inevitably involves mechanical stress, styling agents of this type cannot tolerate any remodeling of the hairstyle.

Available styling agents that permit a certain remodeling (e.g., hair waxes or pastes) are generally based on waxes and have the disadvantage that the degree of hold achievable is low.

Accordingly, the present invention provides a composition for styling keratin fibers having a high setting power (i.e., lends a strong hold to the treated fibers but allows the fibers to be remodeled without loss of the hold). In addition, the compositions should allow hairstyle designs having a high resistance to humidity.

It has now been surprisingly found that this can be achieved by using silica coated with specific copolymers in styling agents.

Accordingly, in one aspect the present invention concerns cosmetic compositions for temporary styling of keratin fibers containing a polysilicic acid in a cosmetically acceptable carrier, wherein the polysilicic acid is coated with at least one copolymer A formed from— at least one monomer A1 according to Formula A1—

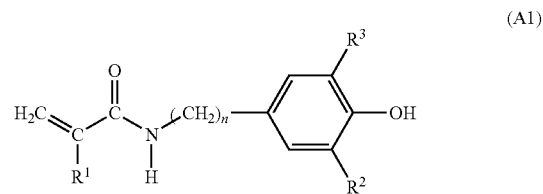

wherein
$R^1$ is H or $CH_3$,
$R^2$ and $R^3$ are each independently H, OH, $C_{1-10}$ alkyl or $C_{1-10}$ alkoxy, with the proviso that at least one of $R^2$ or $R^3$ is OH, and
n is a whole number from 0 to 20; and
at least one monomer A2 according to Formula A2—

wherein
$R^4$ is H or $CH_3$,
Z is O or NH, and
$R^5$ is $C_{1-30}$ alkyl or a $C_{1-30}$ alkylene $C_{1-30}$ alkyl ether group.

Copolymers A are inspired by proteins that mussels utilize in attaching themselves on wet surfaces. They possess a high content of 3,4-dihydroxy-L-phenylalanine. Proteins and synthetic adhesives comprising 3,4-dihydroxy-L-phenylalanine are known for their high adhesive strength on surfaces, even under water. However, the proteins as well as the copolymers A per se are unsuitable for use in styling agents because treated fibers strongly stick together and satisfactory styling results cannot be achieved. It has now been surprisingly found that the high adhesive strength of the copolymers A retained under extremely moist conditions can be used in preparing novel styling agents having special properties if polysilicic acids are coated with the copolymer A and the coated silicic acids are blended into appropriate cosmetic compositions. These styling agents provide good moisture resistance of the obtained hold. In spite of the high hold the hairstyle moreover remains deformable.

Accordingly, inventive cosmetic compositions comprise a polysilicic acid that is coated with at least one copolymer A.

In the context of the present invention, copolymers A formed from monomers A1 and A2 are understood to include only those copolymers that, in addition to polymer units resulting from the incorporation of monomers A1 and A2 into the copolymer, include a maximum of 5 wt. %, preferably a maximum of 1 wt. % of polymer units that trace back to the incorporation of monomers other than A1 and A2. Copolymers A are preferably exclusively formed from polymer units that result from the incorporation of monomers A1 and A2 into the copolymer.

Copolymers A are preferably manufactured from monomers A1 of Formula A1 in which $R^1$ is $CH_3$. Therefore, methacrylamide derivatives are employed.

Monomers A1 of Formula A1 are also preferred, wherein $R^2$ and $R^3$ are each independently H, OH, methyl, ethyl, n-propyl, iso-propyl, n-butyl, iso-butyl, tert.-butyl or n-pentyl, with the proviso that at least one of the groups $R^2$ or $R^3$ is OH. Particularly preferably, $R^2$ and $R^3$ in Formula A1 are each independently H or OH, with the proviso that at least one of the groups $R^2$ or $R^3$ is OH, quite particularly preferably wherein one of the groups $R^2$ or $R^3$ is OH and the other is H.

Finally, monomers A1 of Formula A1 are preferred wherein n is a whole number from 1 to 10, preferably a whole number from 1 to 5, particularly preferably 2.

Copolymers A are particularly preferably manufactured from monomers A1 of Formula A1 wherein $R^1$, $R^2$, $R^3$ and n each possess the just cited preferred and particularly preferred meanings.

Copolymers A are preferably manufactured from monomers A2 of Formula A2 wherein $R^4$ is H.

It is also preferred to employ monomers A2 of Formula A2 wherein Z is O.

Finally, monomers A2 of Formula A2 are preferred wherein $R^5$ is methyl, ethyl, n-propyl, iso-propyl, n-butyl, iso-butyl, tert.-butyl, n-pentyl, methyleneoxy methyl, methyleneoxy ethyl, methyleneoxy n-propyl, methyleneoxy iso-propyl, methyleneoxy n-butyl, methyleneoxy iso-butyl, methyleneoxy tert.-butyl, methyleneoxy n-pentyl, ethyleneoxy methyl, ethyleneoxy ethyl, ethyleneoxy n-propyl, ethyleneoxy iso-propyl, ethyleneoxy n-butyl, ethyleneoxy iso-butyl, ethyleneoxy tert.-butyl, ethyleneoxy n-pentyl, n-propyleneoxy methyl, n-propyleneoxy ethyl, n-propyleneoxy n-propyl, n-propyleneoxy iso-propyl, n-propyleneoxy n-butyl, n-propyleneoxy iso-butyl, n-propyleneoxy tert.-butyl or n-propyleneoxy n-pentyl, wherein monomers A2 of Formula A2 with $R^5$=ethyleneoxy methyl are particularly preferred.

Copolymers A are particularly preferably manufactured from monomers A2 of Formula A2 wherein $R^4$, $R^5$ and Z each possess the just cited preferred and particularly preferred meanings.

Quite particularly preferred copolymers A are formed from the cited particularly preferred monomers A1 and A2.

Consequently, the inventive compositions preferably concern compositions comprising a polysilicic acid that is coated with a copolymer A, wherein the copolymer A is formed from— at least one monomer A1 according to Formula A1—

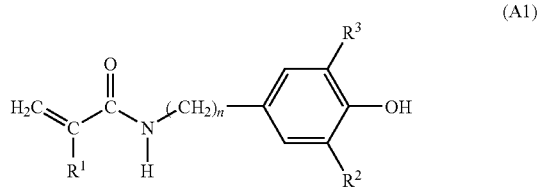

(A1)

wherein
$R^1$ is $CH_3$,
$R^2$ and $R^3$ are each independently H or OH, with the proviso that only one of $R^2$ or $R^3$ is OH, and
n is 2; and
at least one monomer A2 according to Formula A2—

(A2)

wherein
$R^4$ is H,
Z is O, and
$R^5$ is $CH_2$—$CH_2$—O—$CH_3$.

Preferably, copolymer A is formed from 5 to 25 wt. % monomer A1 and 95 to 75 wt. % monomer A2, particularly preferably from 10 to 20 wt. % monomer A1 and 90 to 80 wt. % monomer A2, quite particularly preferably from 15 to 18 wt. % monomer A1 and 85 to 82 wt. % monomer A2.

Preparation of the required monomers and copolymers A is known and described, for example, by H. Lee, B. P. Lee and P. B. Messersmith in *Nature*, Vol. 448, pp. 338-341 (2007).

The polysilicic acid that is coated with copolymer A preferably is pyrogenic silica or precipitated silica.

In a first preferred embodiment, pyrogenic silica is used, preferably pyrogenic silica with a specific BET surface area of 25 to 600 m$^2$/g, wherein the specific BET surface area is determined according to DIN 66131: 1993-07.

The pyrogenic silica preferably has primary particle size of 5 to 200 nm and an agglomerate size of 2 to 15 µm, wherein the primary particle size and the agglomerate size are measured by scanning electron microscopy.

In a second preferred embodiment, precipitated silica is used, preferably precipitated silica with a specific BET surface area of 30 to 800 m$^2$/g, wherein the specific BET surface area is determined according to DIN 66131: 1993-07.

The precipitated silica preferably has primary particle size of 5 to 200 nm and an agglomerate size of 1 to 40 µm, wherein the primary particle size and the agglomerate size are measured by scanning electron microscopy. Primary particle sizes of 5 to 100 nm are particularly preferred.

Coating of the polysilicic acid with copolymer A can be carried out following the dip-coating method with polydimethylsiloxane described by H. Lee, B. P. Lee and P. B. Messersmith in *Nature*, Vol. 448, pp. 338-341 (2007). According to this process, copolymer A is dissolved, for example, in ethanol, wherein the copolymer content is about 1 mg·ml$^{-1}$, the solution is heated to 70° C., and the polysilicic acid is added with stirring. The weight ratio of copolymer to polysilicic acid and the time that the polysilicic acid is in contact with the copolymer solution determines the thickness of the coating of copolymer A onto the polysilicic acid. This coated polysilicic acid can be blended into the styling agent as an ethanolic suspension, wherein its concentration can be adjusted as desired by partially evaporating the alcohol or by adding additional solvent. It is also possible in a first step to completely eliminate the ethanol from the coated polysilicic acid in a rotary evaporator or by filtration and drying, and subsequently blend it into the cosmetic composition.

Of course it is also possible to employ a mixture of a plurality of copolymers A to coat the polysilicic acid, wherein preferably the above cited preferred copolymers A are employed.

Copolymer A-coated polysilicic acids are preferably added into the inventive compositions, wherein the weight ratio of copolymer A to polysilicic acid is 1:1 to 1:1000, preferably 1:10 to 1:500.

Compositions according to the invention contain the copolymer A-coated polysilicic acid preferably in an amount of 0.001 to 40 wt. %, preferably 0.01 to 30 wt. %, particularly preferably 0.1 to 20 wt. % and quite particularly preferably 1.0 to 10 wt. %, based on total weight of the composition.

Compositions according to the invention can additionally include a film-forming and/or setting polymer. However, in a preferred embodiment, the compositions are formulated with the copolymer A-coated polysilicic acid as the sole setting component.

If film forming and/or setting polymers are employed, all polymers typically employed for this purpose in styling agents may be used. Film forming and/or setting polymers can be chosen from amphoteric, non-ionic, anionic and cationic film forming and/or setting polymers.

As polymers are often multifunctional, their functions cannot always be clearly and unequivocally delimited from one another. This is particularly true for film-forming and setting polymers. In the context of the present invention, both film forming as well as setting polymers are referred to. As both properties are not completely independent from one other, the term "setting polymers" is also always understood to mean "film-forming polymers" and vice versa.

Preferred properties of the film forming polymers include film formation. Film forming polymers refer to those polymers that on drying leave a continuous film on the skin, hair or nails. These types of film former can be used in a wide variety of cosmetic products such as make up masks, make up, hair sets, hair sprays, hair gels, hair waxes, hair conditioners, shampoos or nail varnishes. Those products are particularly preferred which are sufficiently soluble in alcohol or water/alcohol mixtures, such that they are present in completely dissolved form in the compositions according to the invention. Film forming polymers can be synthetic or natural in origin.

According to the invention, film forming polymers also refers to polymers that, when used in concentrations of 0.01 to 20 wt. % in aqueous, alcoholic or aqueous alcoholic solution, are able to separate out a transparent polymer film on the hair.

Suitable amphoteric film-forming and/or setting polymers are preferably chosen from copolymers of monomers containing carboxy and/or sulfonic groups, especially acrylic acid, methacrylic acid, itaconic acid, as well as monomers containing amino groups, especially monoalkylaminoalkyl acrylates, dialkylaminoalkyl acrylates, monoalkylaminoalkyl methacrylates, dialkylaminoalkyl methacrylates, monoalkylaminoalkyl acrylamides, dialkylaminoalkyl acrylamides, monoalkylaminoalkyl methacrylamides, dialkylaminoalkyl methacrylamides, and the copolymers of N-octylacrylamide, methyl methacrylate, hydroxypropyl methacrylate, N-tert.-butylaminoethyl methacrylate and acrylic acid.

Particularly preferred amphoteric film-forming and/or setting polymers include N-octylacrylamide/acrylic acid/tert.-butylaminoethyl methacrylate copolymers, preferably the copolymer commercialized by Akzo Nobel SPG LLC under the name Amphomer® (INCI name: Octylacrylamide/Acrylates/Butylaminoethyl Methacrylate Copolymer).

Further exemplary synthetic, film forming, hair setting polymers include homopolymers or copolymers based on at least one of the following monomers: vinyl pyrrolidone, vinyl caprolactam, vinyl esters such as vinyl acetate, vinyl alcohol, acrylamide, methacrylamide, alkyl- and dialkyl acrylamide, alkyl- and dialkyl methacrylamide, alkyl acrylate, alkyl methacrylate, propylene glycol or ethylene glycol, wherein the alkyl groups of these monomers are preferably $C_1$ to $C_7$ alkyl groups, particularly preferably $C_1$ to $C_3$ alkyl groups.

Homopolymers of vinyl caprolactam, vinyl pyrrolidone or N-vinyl formamide may be cited as examples. Further suitable synthetic film forming, hair setting polymers include copolymers of vinyl pyrrolidone and vinyl acetate, terpolymers of vinyl pyrrolidone, vinyl acetate and vinyl propionate, polyacrylamides that, for example, are commercialized under the trade names Akypomine® p 191 by CHEM-Y, Emmerich, or Sepigel® 305 by Seppic; polyvinyl alcohols that are commercialized under the trade names Elvanol® by Du Pont or Vinol® 523/540 by Air Products as well as polyethylene glycol/polypropylene glycol copolymers, commercialised, for example, under the trade name Ucon® by Union Carbide.

Suitable natural film forming polymers include cellulose derivatives (e.g., hydroxypropyl cellulose) with a molecular weight of 30,000 to 50,000 g/mol, commercialized under the trade name Nisso S1® by Lehmann & Voss, Hamburg.

Setting polymers contribute to the hold and/or creation of hair volume and hair body of the whole hairstyle. These so-called setting polymers are also film-forming polymers and therefore are generally typical substances for styling hair treatment compositions such as hair sets, hair foams, hair waxes, hair sprays. The film formation can be in completely selected areas and bond only some fibers together.

Substances that additionally confer hydrophobic properties to the hair are preferred because they reduce the tendency of the hair to absorb moisture (i.e., water). This reduces sagging of the tresses of hair, thereby ensuring a long-lasting style configuration and retention. The so-called curl-retention test is frequently used as the test method for this. Moreover, these polymeric substances can be successfully incorporated in leave-on and rinse-off hair conditioners or shampoos. As polymers are often multifunctional (i.e., they show a plurality of desired end-use effects), a large number of polymers are found in many of the groups subdivided according to the mode of action, as well as in the CTFA Handbook.

When the inventive compositions comprise film-forming and/or setting polymers, they are added preferably in an amount of 0.01 to 20 wt. %, preferably 0.1 to 15 wt. %, based on total weight of the hair setting agent. Of course, a plurality of film forming and/or setting polymers can be included, wherein the total amount of film-forming and/or setting polymers is, however preferably at a maximum of 20 wt. %.

Compositions according to the invention typically include the polymers in a cosmetically acceptable carrier.

Preferred cosmetically acceptable carriers include aqueous, alcoholic or aqueous alcoholic media containing preferably at least 10 wt. % water, based on total composition. In particular, lower alcohols containing 1 to 4 carbon atoms such as ethanol and isopropanol, which are usually used for cosmetic purposes, can be used.

Organic solvents or mixture of solvents with a boiling point of less than 400° C. can be used as additional co-solvents in an amount of 0.1 to 15 weight percent, preferably 1 to 10 weight percent, based on total weight of the agent. Particularly suitable additional co-solvents include unbranched or branched hydrocarbons such as pentane, hexane, and isopentane, and cyclic hydrocarbons such as cyclopentane and cyclohexane. Additional, particularly preferred water-soluble solvents are glycerin, ethylene glycol and propylene glycol in an amount of up to 30 weight percent based on total weight of the agent.

The agents preferably have a pH in the range of 2 to 11. The pH range is particularly preferably from 2 to 8. In the context of this publication, pH data refer to the pH at 25° C. unless otherwise stated.

Compositions according to the invention can additionally include auxiliaries and additives typically incorporated into styling agents.

In particular, care substances may be mentioned as suitable auxiliaries and additives.

For example, silicone oil and/or silicone gum can be employed as the care substance. In a particular embodiment, the compositions contain at least one silicone oil and/or a silicone gum.

Suitable silicone oils or silicone gums according to the invention include dialkyl and alkylarylsiloxanes such as dimethylpolysiloxane and methylphenylpolysiloxane, as well as their alkoxylated, quaternized or also anionic derivatives. Cyclic and linear polydialkylsiloxanes, their alkoxylated and/or aminated derivatives, dihydroxypolydimethylsiloxanes and polyphenylalkylsiloxanes are preferred.

Silicone oils provide a variety of effects. For example, they simultaneously influence dry and wet combability, the feel of dry and wet hair, as well as the gloss. The term "silicone oils" is understood by the person skilled in the art to refer to organosilicon compounds having a plurality of structures. These include dimethiconols (S1). Dimethiconols can be linear, branched, cyclic, or cyclic and branched. Linear dimethiconols can be represented by the following structural formula (S1-I)—

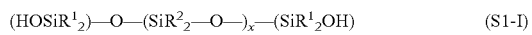
(S1-I)

Branched dimethiconols can be represented by the following structural formula (S1-II)—

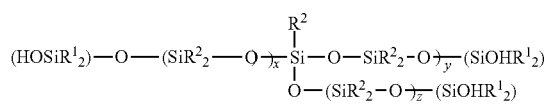
(S1-II)

$R^1$ and $R^2$ are each independently hydrogen, a methyl group, a $C_2$ to $C_{30}$ linear, saturated or unsaturated hydrocarbon group, a phenyl group and/or an aryl group. The numbers x, y and z are whole numbers and each independently range from 0 to 50,000. Molecular weights of the Dimethiconols lie from 1000 D to 10,000,000 D. Viscosities range from 100 to 10,000,000 cPs, measured at 25° C. with a glass capillary viscosimeter following the Dow Corning Corporate Test Method CTM 0004 of 20 Jul. 1970. Preferred viscosities are from 1000 to 5,000,000 cPs, quite particularly preferred viscosities are from 10,000 to 3,000,000 cPs. The most preferred range is from 50,000 to 2,000,000 cPs.

Dimethicones (S2) form the second group of silicones that can be used according to the invention. They can be linear, branched, cyclic, or cyclic and branched. Linear dimethicones can be represented by the following structural formula (S2-I)—

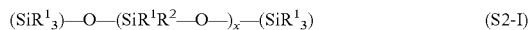
(S2-I)

Branched dimethicones can be represented by the structural formula (S2-II):

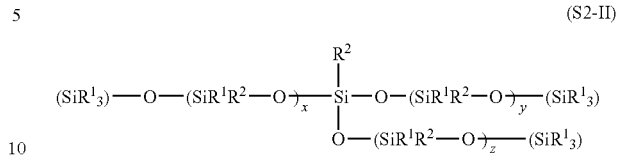
(S2-II)

$R^1$ and $R^2$ are each independently hydrogen, a methyl group, a $C_2$ to $C_{30}$ linear, saturated or unsaturated hydrocarbon group, a phenyl group and/or an aryl group. Particularly preferably $R^1$ and $R^2$ is methyl. The numbers x, y and z are whole numbers and each independently range from 0 to 50,000. Molecular weights of the dimethicones lie from 1000 D to 10,000,000 D. Viscosities range from 100 to 10,000,000 cPs, measured at 25° C. with a glass capillary viscosimeter following the Dow Corning Corporate Test Method CTM 0004 of 20 Jul. 1970. Preferred viscosities are from 1000 to 5,000,000 cPs, quite particularly preferred viscosities are from 10,000 to 3,000,000 cPs. Quite particularly preferably, the viscosity is in the range from 50,000 to 2,000,000 cPs.

Dimethicone copolyols (S3) form a further group of suitable silicones. Dimethicone copolyols can be represented by the following structural formulae—

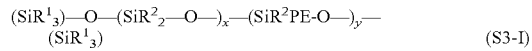
(S3-I)

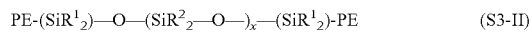
(S3-II)

Branched dimethicone copolyols can be represented by the following structural Formula (S3-III)—

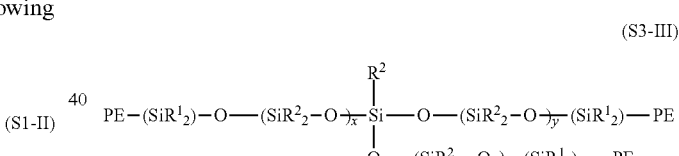
(S3-III)

or by structural Formula (S3-IV)—

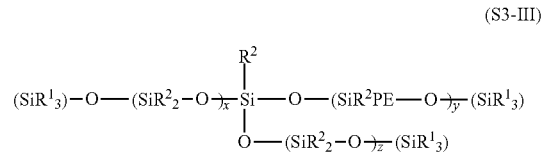
(S3-III)

$R^1$ and $R^2$ are each independently hydrogen, a methyl group, a $C_2$ to $C_{30}$ linear, saturated or unsaturated hydrocarbon group, a phenyl group and/or an aryl group. Preferably $R^1$ and $R^2$ are methyl. PE refers to a polyoxyalkylene group. Preferred polyoxyalkylene groups are derived from ethylene oxide, propylene oxide and glycerin. The numbers x, y and z are whole numbers and each independently range from 0 to 50,000. Molecular weights of the dimethicones lie from 1000 D to 10,000,000 D. Viscosities range from 100 to 10,000,000 cPs, measured at 25° C. with a glass capillary viscosimeter following the Dow Corning Corporate Test Method CTM 0004 of 20 Jul. 1970. Preferred viscosities are from 1000 D to 5,000,000 cPs, quite particularly preferred viscosities are from 10,000 D to 3,000,000 cPs. The most preferred range is from 50,000 D to 2,000,000 cPs.

Suitable dimethicone copolyols are commercially available and are marketed, for example, by Dow Corning under the trade name Dow Corning® 5330 Fluid.

Naturally, according to the invention, dimethiconols, dimethicones and/or dimethicone copolymers can already be present as an emulsion. The corresponding emulsions of the dimethiconols, dimethicones and/or dimethicone copolymers can be produced both after the production of the corresponding dimethiconols, dimethicones and/or dimethicone copolymers from these and the usual emulsification processes known to the person skilled in the art. Cationic, anionic, non-ionic or zwitterionic surfactants and emulsifiers can be used as auxiliaries and adjuvants for the production of the corresponding emulsions. Naturally, emulsions of the dimethiconols, dimethicones and/or dimethicone copolymers can also be produced directly by an emulsion polymerization process. These types of processes are also well known to the person skilled in the art.

When dimethiconols, dimethicones and/or dimethicone copolymers are used as an emulsion, then according to the invention, the droplet size of emulsified particles ranges from 0.01 to 10,000 μm, preferably 0.01 to 100 μm, particularly preferably 0.01 to 20 μm and quite particularly preferably 0.01 to 10 μm. Particle size is determined by the light scattering method.

If branched dimethiconols, dimethicones and/or dimethicone copolymers are used, then it is understood that the branching is greater than a fortuitous branching that accidentally results from impurities in the respective monomers. Accordingly, in the context of the present invention, the degree of branching is understood to be greater than 0.01% for branched dimethiconols, dimethicones and/or dimethicone copolymers. The degree of branching is preferably greater than 0.1%, and quite particularly preferably greater than 0.5%. The degree of branching is determined from the ratio of unbranched monomers to branched monomers (i.e., the amount of tri and tetrafunctional siloxanes). According to the invention, both low-branched as well as highly branched Dimethiconols, Dimethicones and/or Dimethicone copolymers can be quite particularly preferred.

Further suitable silicones include amino functional silicones (S4), especially those silicones compiled under the INCI name Amodimethicone. These refer to silicones having at least one, optionally substituted, amino group.

Such silicones can be described, for example, by Formula (S4-I)—

$$M(R_aQ_bSiO_{(4-a-b)/2})_x(R_cSiO_{(4-c)/2})_yM \quad (S4\text{-}I)$$

wherein R is a hydrocarbon or a hydrocarbon group with 1 to 6 carbon atoms, Q is a polar group of the general formula —R$^1$Z, wherein R$^1$ is a divalent, linking group bonded to hydrogen and the group Z, made up of carbon atoms and hydrogen atoms, carbon-, hydrogen- and oxygen atoms or carbon-, hydrogen- and nitrogen atoms, and Z is an organic amino functionalized group having at least one amino functional group; "a" is a value in the range of about 0 to about 2, "b" is a value in the range of about 1 to about 3, "a"+"b" is less than or equal to 3, and "c" is a number in the range of about 1 to about 3, and x is a number in the range of 1 to about 2000, advantageously from about 3 to about 50 and most preferably from about 3 to about 25, and y is a number in the range of about 20 to about 10,000, advantageously from about 125 to about 10,000 and most preferably from about 150 to about 1000, and M is a suitable silicone end-group as known from the prior art, preferably trimethylsiloxy.

Z is an organic, amino functional group having at least one functional amino group. A possible formula for Z is NH(CH$_2$)$_z$NH$_2$, wherein z is a whole number from 1 to 50. Another possible formula for Z is —NH(CH$_2$)$_z$NH(CH$_2$)$_{zz}$, in which both z and zz are each independently a whole number from 1 to 50, wherein this structure includes diamino ring structures such as piperazinyl. Particularly preferably, Z is a —NHCH$_2$CH$_2$NH$_2$ group. Another possible formula for Z is —N(CH$_2$)$_z$NX$^1$X$^2$ or —NX$^1$X$^2$, in which X$^1$ and X$^2$ are each independently hydrogen or a hydrocarbon group containing 1 to about 6 carbon atoms.

Q stands quite particularly preferably for a polar, amino functional group according to the Formula—

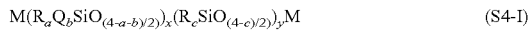
—CH$_2$CH$_2$CH$_2$NHCH$_2$CH$_2$NH$_2$

The molar ratio of the R$_a$Qb SiO$_{(4-a-b)/2}$ units to the R$_c$SiO$_{(4-c)/2}$ units is in the range from about 1:2 to 1:65, preferably from about 1:5 to about 1:65 and particularly preferably from about 1:15 to about 1:20. If one or a plurality of silicones of the above Formula is added, then the different variable substituents in the above Formula for the different silicone components that are present in the silicone mixture can be different.

Preferred amino functional silicones correspond to Formula (S4-II)—

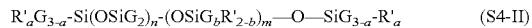
$$R'_aG_{3-a}\text{-}Si(OSiG_2)_n\text{-}(OSiG_bR'_{2-b})_m\text{—}O\text{—}SiG_{3-a}\text{-}R'_a \quad (S4\text{-}II)$$

wherein
G is —H, a phenyl group, —OH, —O—CH$_3$, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)CH$_2$CH$_3$, —C(CH$_3$)$_3$;

a is a number from 0 to 3, particularly 0;

b is a number from 0 to 1, particularly 1;

m and n are numbers whose sum (m+n) is from 1 to 2000, preferably from 50 to 150, wherein n preferably is a value from 0 to 1999, particularly 49 to 149, and m preferably is a value from 1 to 2000, particularly 1 to 10;

R' is a monovalent group selected from —N(R")—CH$_2$—CH$_2$—N(R")$_2$, —N(R")$_2$, —N$^+$(R")$_3$A$^-$, —N$^+$H(R")$_2$A$^-$, —N$^+$H$_2$(R")A$^-$, —N(R")—CH$_2$—CH$_2$—N$^+$R"H$_2$A$^-$, wherein each R" is the same or different groups from the group —H, -phenyl, -benzyl, the C$_{1\text{-}20}$ alkyl groups, preferably —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)CH$_2$CH$_3$, —C(CH$_3$)$_3$, and A$^-$ represents an anion that is preferably selected from chloride, bromide, iodide or methosulfate Particularly preferred amino functional silicones correspond to Formula (S4-III)—

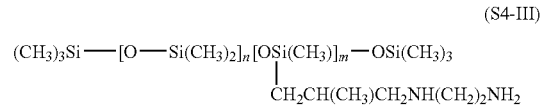

(S4-III)

$$(CH_3)_3Si\text{—}[O\text{—}Si(CH_3)_2]_n[OSi(CH_3)]_m\text{—}OSi(CH_3)_3$$
$$|$$
$$CH_2CH(CH_3)CH_2NH(CH_2)_2NH_2$$

wherein m and n are numbers whose sum (m+n) is from 1 to 2000, preferably from 50 to 150, wherein n preferably is a value from 0 to 1999, particularly from 49 to 149, and m preferably is a value from 1 to 2000, particularly 1 to 10.

These silicones are designated according to the INCI nomenclature as Trimethylsilylamodimethicones.

Further amino functional silicones according to Formula (S4-IV) are particularly preferred—

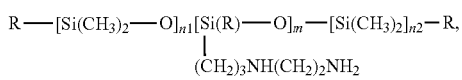

(S4-IV)

wherein R is —OH, —O—CH₃ or a —CH₃ group and m, n1 and n2 are numbers whose sum (m+n1+n2) is from 1 to 2000, preferably 50 to 150, wherein the sum (n1+n2) preferably is a value from 0 to 1999, particularly from 49 to 149, and m preferably is a value from 1 to 2000, particularly 1 to 10.

These silicones are designated as Amodimethicones according to INCI nomenclature and are available, for example, in the form of an emulsion as the commercial product Dow Corning® 949 in a mixture with a cationic and a non-ionic surfactant.

Preferably, those amino functional silicones are employed having an amine number of 0.25 meq/g or greater, preferably 0.3 meq/g or greater, and particularly preferably 0.4 meq/g or greater. The amine number represents milli-equivalents of amine per gram of the amino functional silicone. It can be measured by titration and is also reported with the unit mg KOH/g.

Further suitable silicones include—
oligomeric polydimethylcyclosiloxanes (INCI name: Cyclomethicones), especially the tetrameric and the pentameric compound, which are commercialized as the products DC 245 Fluid, DC 344 or DC 345 by Dow Corning,
hexamethyldisiloxane (INCI name: Hexamethyldisiloxane), for example, the product marketed under the trade name Abil® K 520,
polyphenylmethylsiloxane (INCI name: Phenyl Trimethicone), for example, the commercial product DC 556 Cosmetic Grade Fluid from Dow Corning,
esters and partial esters of silicone-glycol copolymers, as are commercialized, for example, by Fanning Company under the trade name Fancorsil® LIM (INCI name: Dimethicone Copolyol Meadowfoamate),
anionic silicone oils such as the product Dow Corning® 1784.

According to a preferred embodiment, the composition according to the invention includes at least two different silicone derivatives, in particular a combination of a volatile and a non-volatile silicone. In the context of the invention, volatile silicones are those that exhibit a volatility that is the same or greater than the volatility of the cyclic, pentameric dimethylsiloxane. Such combinations are also available as commercial products (e.g., Dow Corning® 1401, Dow Corning® 1403 and Dow Corning® 1501, each being mixtures of a Cyclomethicone and a Dimethiconol).

Preferred mixtures of different silicones include dimethicones and dimethiconols, linear dimethicones and cyclic dimethiconols. A quite particularly preferred mixture of silicones consists of at least one cyclic dimethiconol and/or dimethicone, at least one additional non-cyclic dimethicone and/or dimethiconol as well as at least one amino functional silicone.

If different silicones are used as a mixture, then the mixing ratio can be varied over a wide range. Preferably, however, all of the silicones used in the mixture are employed in a ratio of 5:1 to 1:5 in the case of a binary mixture. A ratio of 3:1 to 1:3 is particularly preferred. Quite particularly preferred mixtures comprise as far as possible all silicones comprised in the mixture in a ratio of about 1:1, each based on the added quantities in wt.-%.

The compositions preferably contain silicones in amounts of 1 to 25 wt. %, particularly preferably in amounts of 5 to 20 wt. % and particularly preferably in amounts of 7-15 wt. %, based on total weight of the composition.

Although compositions according to the invention preferably comprise a silicone derivative as the conditioning component, it is also possible that the composition comprises at least one conditioner from another compound class instead of or in addition to a silicone component.

The composition can comprise, for example, at least one protein hydrolyzate and/or one of its derivatives as a care substance of another compound class.

Protein hydrolyzates are product mixtures obtained by acid-, base- or enzyme-catalyzed degradation of proteins (albumins). According to the invention, the term "protein hydrolyzates" is also understood to mean total hydrolyzates as well as individual amino acids and their derivatives as well as mixtures of different amino acids. Furthermore, according to the invention, polymers built up from amino acids and amino acid derivatives are understood to be included in the term protein hydrolyzates. The latter include for example polyalanine, polyasparagine, polyserine etc. Additional examples of usable compounds according to the invention are L-alanyl-L-proline, polyglycine, glycyl-L-glutamine or D/L-methionine-S-methyl sulfonium chloride. Of course, β-amino acids and their derivatives, like β-alanine, anthranilic acid or hippuric acid, can also be added according to the invention. Molecular weight of the protein hydrolyzates utilizable according to the invention ranges from about 75, the molecular weight of glycine, to about 200,000. Preferably, the molecular weight is 75 to 50,000, and quite particularly preferably 75 to 20,000 Dalton.

According to the invention, the added protein hydrolyzates can be vegetal, animal, marine or synthetic in origin. Animal protein hydrolyzates include elastin, collagen, keratin, silk protein, and milk protein hydrolyzates, which can also be present in the form of their salts. Such products are marketed, for example, under the trade names Dehylan® (Cognis), Promois® (Interorgana), Collapuron® (Cognis), Nutrilan® (Cognis), Gelita-Sol® (Deutsche Gelatine Fabriken Stoess & Co), Lexein® (Inolex), Sericin (Pentapharm) and Kerasol® (Croda).

Protein hydrolyzates of vegetal origin (e.g., soya-, almond-, pea-, potato- and wheat protein hydrolyzates) are available, for example, under the trade names Gluadin® (Cognis), DiaMin® (Diamalt), Lexein® (Inolex), Hydrosoy® (Croda), Hydrolupin® (Croda), Hydrosesame® (Croda), Hydrotritium® (Croda) and Crotein® (Croda).

Although it is preferred to add the protein hydrolyzates as such, optionally other mixtures containing amino acids can used in their place. Likewise, it is possible to add derivatives of protein hydrolyzates (e.g., in the form of their fatty acid condensation products). Such products are marketed, for example, under the trade names Lamepon® (Cognis), Lexein® (Inolex), Crolastin® (Croda), Crosilk® (Croda) or Crotein® (Croda).

Naturally, the teaching according to the invention includes all isomeric forms, such as cis/trans isomers, diastereoisomers and chiral isomers.

According to the invention, it is also possible to employ a mixture of a plurality of protein hydrolyzates.

Compositions according to the invention contain protein hydrolyzates, for example, in concentrations of 0.01 wt. % to 20 wt. %, preferably 0.05 wt. % up to 15 wt. % and quite particularly preferably in amounts of 0.05 wt. % up to 5 wt. %, each based on the total end-use preparation.

In addition, cationic surfactants are suitable as care substances of another class of compounds.

According to the invention, cationic surfactants of the type quaternary ammonium compounds, the esterquats and the amido amines are preferred. Preferred quaternary ammonium compounds are ammonium halides, particularly chlorides and bromides, such as alkyltrimethylammonium chlorides, dialkyldimethylammonium chlorides and trialkylmethylammonium chlorides (e.g., cetyltrimethylammonium chloride, stearyltrimethylammonium chloride, distearyldimethylammonium chloride, lauryldimethylammonium chloride, lauryldimethylbenzylammonium chloride and tricetylmethylammonium chloride, as well as the imidazolium compounds known under the INCI names Quaternium-27 and Quaternium-83. The long alkyl chains of the above-mentioned surfactants have preferably 10 to 18 carbon atoms.

Esterquats are known compounds having at least one ester function and also a quaternary ammonium group as structural elements. Preferred esterquats include quaternized ester salts of fatty acids with triethanolamine, quaternized ester salts of fatty acids with diethanolalkylamines and quaternized ester salts of fatty acids with 1,2-dihydroxypropyldialkylamines. Such products are marketed, for example, under the trade names Stepantex®, Dehyquart® and Armocare®. The products Armocare® VGH-70, an N,N-bis(2-palmitoyloxyethyl) dimethylammonium chloride, as well as Dehyquart® F-75, Dehyquart® C-4046, Dehyquart® L80 and Dehyquart® AU 35 are examples of such esterquats.

The alkylamido amines are normally manufactured by amidation of natural or synthetic fatty acids and fatty acid fractions with dialkylamino amines. According to the invention, a particularly suitable compound from this substance group is stearamidopropyldimethylamine, commercially available under the designation Tegamid® S18.

The inventive compositions preferably include cationic surfactants in quantities of 0.05 to 10 wt. %, based on the total end-use preparation. Quantities of 0.1 to 5 wt. % are particularly preferred.

Conditioning polymers are also suitable conditioners. It is worth mentioning here that some conditioning polymers also exhibit film-forming and/or setting properties, and consequently can also be named in the listing of suitable film-forming and/or setting polymers.

One group of conditioning polymers are the cationic polymers. Cationic polymers are understood to mean polymers having a group in the main chain and/or side chain which can be "temporarily" or "permanently" cationic. "Permanently cationic" refers, according to the invention, to those polymers, which independently of the pH of the medium have a cationic group. These are generally polymers, which comprise a quaternary nitrogen atom, in the form of an ammonium group, for example. Preferred cationic groups are quaternary ammonium groups. In particular, those polymers in which the quaternary ammonium groups are bonded through a $C_{1-4}$ hydrocarbon group to a polymer backbone of acrylic acid, methacrylic acid or their derivatives, have proved to be particularly suitable.

Homopolymers of the general formula (G1-I)—

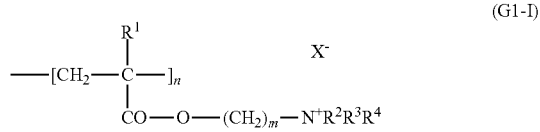

(G1-I)

wherein $R^1$ is —H or —$CH_3$; $R^2$, $R_3$ and $R^4$ are each independently $C_{1-4}$ alkyl, -alkenyl or -hydroxyalkyl groups; m=1, 2, 3 or 4; n is a natural number; and $X^-$ is a physiologically compatible organic or inorganic anion, as well as copolymers, essentially consisting of the monomer units listed in formula (G1-I) as well as non-ionic monomer units, are particularly preferred cationic polymers. Regarding these polymers, those that are preferred in accordance with the invention meet at least one of the following conditions—

$R^1$ is a methyl group $R^2$, $R^3$ and $R^4$ are methyl groups m is the value 2.

Exemplary physiologically compatible counter ions $X^-$ include halide ions, sulfate ions, phosphate ions, methosulfate ions as well as organic ions such as lactate, citrate, tartrate and acetate ions. Halide ions are preferred, particularly chloride.

A particularly suitable homopolymer is the optionally crosslinked poly(methacryloyloxyethyltrimethylammonium chloride) with the INCI name Polyquaternium-37. Crosslinking can be effected, when desired, with the help of olefinically polyunsaturated compounds, for example divinylbenzene, tetraallyloxyethane, methylene bisacrylamide, diallyl ether, polyallyl polyglyceryl ether, or allyl ethers of sugars or sugar derivatives such as erythritol, pentaerythritol, arabitol, mannitol, sorbitol, sucrose or glucose. Methylene bisacrylamide is a preferred crosslinking agent.

The homopolymer is preferably employed in the form of a non-aqueous polymer dispersion that should have a polymer content of not less than 30 wt. %. Such polymer dispersions are commercially available under the names Salcare® SC 95 (ca. 50% polymer content, additional components: mineral oil (INCI name: Mineral Oil) and tridecyl-polyoxypropylene polyoxyethylene ether (INCI name: PPG-1-Trideceth-6)) and Salcare® SC 96 (ca. 50% polymer content, additional components: mixture of diesters of propylene glycol with a mixture of caprylic- and capric acid (INCI name: Propylene Glycol Dicaprylate/Dicaprate) and tridecyl-polyoxypropylene polyoxyethylene ether (INCI name: PPG-1-Trideceth-6)).

Copolymers with monomer units according to formula (G1-I) preferably comprise acrylamide, methacrylamide, $C_{1-4}$ alkyl esters of acrylic acid and $C_{1-4}$ alkyl esters of methacrylic acid as the non-ionic monomer units. Acrylamide is particularly preferred among these non-ionic monomers. These copolymers can also be crosslinked, as in the case of the above-described homopolymers. An inventively preferred copolymer is the crosslinked acrylamide/methacryloyloxyethyltrimethylammonium chloride copolymer. Such copolymers, in which the monomers are present in a weight ratio of about 20:80, are commercially available as a ca. 50% conc. non-aqueous polymer dispersion under the trade name Salcare® SC 92.

Further preferred cationic polymers include— quaternized cellulose derivatives, commercially available under the trade names Celquat® and Polymer JR®. The compounds Celquat® H 100, Celquat® L 200 and Polymer JR®400 are preferred quaternized cellulose derivatives, cationic alkyl polyglycosides according to DE-PS 44 13 686, cationized honey, for example the commercial product Honeyquat® 50, cationic guar derivatives, such as in particular the products marketed under the trade names Cosmedia® Guar and Jaguar®, polysiloxanes with quaternary groups, such as, for example, the commercially available products Q2-7224

(manufacturer: Dow Corning; a stabilized trimethylsilylamodimethicone), Dow Corning® 929 emulsion (comprising a hydroxylamino modified silicone, also referred to as amodimethicone), SM-2059 (manufacturer: General Electric), SLM-55067 (manufacturer: Wacker), and Abil®-Quat 3270 and 3272 (manufacturer: Th. Goldschmidt; diquaternary polydimethylsiloxanes, Quaternium-80), polymeric dimethyldiallylammonium salts and their copolymers with esters and amides of acrylic acid and methacrylic acid. The commercially available products Merquat®100 (poly(dimethyldiallylammonium chloride)) and Merquat®550 (dimethyldiallylammonium chloride acrylamide copolymer) are examples of such cationic polymers, copolymers of vinyl pyrrolidone with quaternized derivatives of dialkylaminoalkyl acrylate and dialkylaminoalkyl methacrylate, such as, for example vinyl pyrrolidone-dimethylaminoethyl methacrylate copolymers quaternized with diethyl sulfate. Such compounds are commercially available under the trade names Gafquat®734 and Gafquat®755.

Vinyl pyrrolidone vinyl imidazolium methochloride copolymers, as are offered under the trade names Luviquat® FC 370, FC 550, FC 905 and HM 552, quaternized polyvinyl alcohol as well as polymers containing quaternary nitrogen atoms in the main polymer chain, known under the names Polyquaternium 2, Polyquaternium 17, Polyquaternium 18 and Polyquaternium 27.

Polymers designated as Polyquaternium-24 (commercial product e.g. Quatrisoft® LM 200) can also be employed as cationic polymers. The copolymers of vinyl pyrrolidone are also usable according to the invention, such as the commercially available products Copolymer 845 (manufacturer: ISP), Gaffix® VC 713 (manufacturer: ISP), Gafquat® ASCP 1011, Gafquat®HS 110, Luviquat® 8155 and Luviquat® MS 370.

Further suitable cationic polymers according to the invention are the "temporarily cationic" polymers. These polymers usually have an amino group present at specific pH values as the quaternary ammonium group and is thus cationic. Chitosan and its derivatives, such as the commercially available Hydagen® CMF, Hydagen® HCMF, Kytamer® PC and Chitolam® NB/101, are preferred.

Inventively preferred cationic polymers include cationic cellulose derivatives and chitosan and its derivatives, in particular the commercial products Polymer® JR 400, Hydagen® HCMF and Kytamer® PC, cationic guar derivatives, cationic honey derivatives, in particular the commercial product Honeyquat® 50, cationic alkyl polyglycosides and polymers of the type Polyquaternium-37.

In addition, cationized protein hydrolyzates are considered as cationic polymers, wherein the base protein hydrolyzate can originate from animals, for example from collagen, milk or keratin, from plants, for example from wheat, maize, rice, potatoes, soya or almonds, from marine life, for example from fish collagen or algae, or from biotechnologically obtained protein hydrolyzates. The inventive cationic derivatives based on protein hydrolyzates can be obtained from corresponding proteins by chemical, particularly alkaline or acidic hydrolysis, by enzymatic hydrolysis and/or a combination of both types of hydrolysis. Hydrolysis of proteins generally produces a protein hydrolyzate with a molecular weight distribution from about 100 Daltons up to several thousand Daltons. Cationic protein hydrolyzates are preferred whose base protein content has a molecular weight of 100 to 25,000 Daltons, preferably 250 to 5000 Daltons. Moreover, cationic protein hydrolyzates are understood to include quaternized amino acids and their mixtures. Quaternization of the protein hydrolyzates or the amino acids is often carried out using quaternary ammonium salts such as N,N-dimethyl-N-(n-alkyl)-N-(2-hydroxy-3-chloro-n-propyl) ammonium halides. Moreover, cationic protein hydrolyzates can also be further derivatized. Typical examples of inventive cationic protein hydrolyzates and derivatives thereof include the following commercially available products under their INCI names: Cocodimonium Hydroxypropyl Hydrolyzed Collagen, Cocodimonium Hydroxypropyl Hydrolyzed Casein, Cocodimonium Hydroxypropyl Hydrolyzed Collagen, Cocodimonium Hydroxypropyl Hydrolyzed Hair Keratin, Cocodimonium Hydroxypropyl Hydrolyzed Keratin, Cocodimonium Hydroxypropyl Hydrolyzed Rice Protein, Cocodimonium Hydroxypropyl Hydrolyzed Soy Protein, Cocodimonium Hydroxypropyl Hydrolyzed Wheat Protein, Hydroxypropyl Arginine Lauryl/Myristyl Ether HCl, Hydroxypropyltrimonium Gelatin, Hydroxypropyltrimonium Hydrolyzed Casein, Hydroxypropyltrimonium Hydrolyzed Collagen, Hydroxypropyltrimonium Hydrolyzed Conchiolin Protein, Hydroxypropyltrimonium Hydrolyzed Keratin, Hydroxypropyltrimonium Hydrolyzed Rice Bran Protein, Hydroxypropyltrimonium Hydrolyzed Soy Protein, Hydroxypropyl Hydrolyzed Vegetable Protein, Hydroxypropyltrimonium Hydrolyzed Wheat Protein, Hydroxypropyltrimonium Hydrolyzed Wheat Protein/Siloxysilicate, Laurdimonium Hydroxypropyl Hydrolyzed Soy Protein, Laurdimonium Hydroxypropyl Hydrolyzed Wheat Protein, Laurdimonium Hydroxypropyl Hydrolyzed Wheat Protein/Siloxysilicate, Lauryldimonium Hydroxypropyl Hydrolyzed Casein, Lauryldimonium Hydroxypropyl Hydrolyzed Collagen, Lauryldimonium Hydroxypropyl Hydrolyzed Keratin, Lauryldimonium Hydroxypropyl Hydrolyzed Soy Protein, Steardimonium Hydroxypropyl Hydrolyzed Casein, Steardimonium Hydroxypropyl Hydrolyzed Collagen, Steardimonium Hydroxypropyl Hydrolyzed Keratin, Steardimonium Hydroxypropyl Hydrolyzed Rice Protein, Steardimonium Hydroxypropyl Hydrolyzed Soy Protein, Steardimonium Hydroxypropyl Hydrolyzed Vegetable Protein, Steardimonium Hydroxypropyl Hydrolyzed Wheat Protein, Steartrimonium Hydroxyethyl Hydrolyzed Collagen, Quaternium-76 Hydrolyzed Collagen, Quaternium-79 Hydrolyzed Collagen, Quaternium-79 Hydrolyzed Keratin, Quaternium-79 Hydrolyzed Milk Protein, Quaternium-79 Hydrolyzed Soy Protein, Quaternium-79 Hydrolyzed Wheat Protein.

Cationic protein hydrolyzates and derivatives based on plants are quite particularly preferred.

Preferably employed amphoteric polymers are such polymers formed from—

(a) Monomers with quaternary ammonium groups according to general Formula (II)—

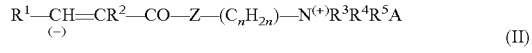

(II)

wherein $R^1$ and $R^2$ are each independently hydrogen or a methyl group, and $R^3$, $R^4$ and $R^5$ are each independently alkyl groups with 1 to 4 carbon atoms, Z is an NH-group or an oxygen atom, n is a whole number from 2 to 5, and $A^{(-)}$ is the anion of an organic or inorganic acid; and (b) Monomeric carboxylic acids according to general formula (III)—

(III)

wherein $R^6$ and $R^7$ are each independently hydrogen or a methyl group.

According to the invention, these compounds can be both added directly as well as in salt form, the latter being obtained by neutralization of the polymer with an alkali hydroxide, for example. Quite particularly preferred are such polymers, which incorporate monomers of type (a), in which $R^3$, $R^4$ and $R^5$ are methyl groups, Z is an NH-group and $A^{(-)}$ is a halide, methoxysulfate or ethoxysulfate ion; acrylamido propyltrimethylammonium chloride is a particularly preferred monomer (a). Acrylic acid is preferably used as the monomer (b) in the cited polymers.

The inventive compositions preferably comprise conditioning, cationic and/or amphoteric polymers in a quantity of 0.01 to 5 wt. %, particularly in a quantity of 0.1 to 2 wt. %, in each case based on the total weight of the end-use preparation.

Compositions according to the invention can further comprise at least one vitamin, one provitamin, one vitamin precursor and/or one of their derivatives as the conditioner.

According to the invention, such vitamins, provitamins and vitamin precursors are preferred which are normally classified in the groups A, B, C, E, F and H.

Substances designated as vitamin A includes retinol (vitamin $A_1$) as well as 3,4-didehydroretinol (vitamin $A_2$). β-Carotene is the provitamin of retinol. Examples of suitable vitamin A components according to the invention are vitamin A acid and its esters, vitamin A aldehyde and vitamin A alcohol as well as its esters such as the palmitate and acetate. The compositions preferably comprise the vitamin A components in amounts of 0.05 to 1 wt. %, based on the total application preparation.

The compositions according to the invention preferably comprise vitamins, provitamins and vitamin precursors from groups A, B, C, E and H.

Panthenol, pantolactone, pyridoxine and its derivatives as well as nicotinamide and biotin are especially preferred.

D-panthenol is quite particularly preferably employed as a conditioner, optionally in combination with at least one of the abovementioned silicone derivatives.

Compositions according to the invention can further comprise at least one plant extract as a conditioner.

Usually, these extracts are manufactured by extraction of the whole plant. In individual cases, however, it can also be preferred to produce the extracts solely from blossoms and/or leaves of the plant.

According to the invention, extracts from green tea, oak bark, stinging nettle, hamamelis, hops, henna, camomile, burdock root, field horsetail, hawthorn, linden flowers, almonds, aloe vera, spruce needles, horse chestnut, sandal wood, juniper, coconut, mango, apricot, lime, wheat, kiwi, melon, orange, grapefruit, sage, rosemary, birch, malva, lady's smock, common yarrow, thyme, lemon balm, rest-harrow, coltsfoot, marshmallow (althaea), meristem, ginseng and ginger are preferred.

Extracts from green tea, oak bark, stinging nettle, hamamelis, hops, camomile, burdock root, hawthorn, linden flowers, almonds, aloe vera, coconut, mango, apricot, lime, wheat, kiwi, melon, orange, grapefruit, sage, rosemary, birch, lady's smock, common yarrow, rest-harrow, meristem, ginseng and ginger are particularly preferred.

Extracts of green tea, almonds, aloe vera, coconut, mango, apricot, lime, wheat, kiwi and melon are quite particularly suitable.

Ectoin or ectoin derivatives, allantoin, taurine and/or bisabolol are also suitable conditioners.

Oil bodies are also suitable as a conditioner.

Natural and synthetic cosmetic oil bodies include—

Vegetal oils. Examples of such oils are sunflower oil, olive oil, soya oil, rapeseed oil, almond oil, jojoba oil, orange oil, wheat germ oil, peach stone oil and the liquid parts of coconut oil. Other triglyceride oils such as the liquid fractions of beef tallow as well as synthetic triglyceride oils are also suitable, however.

liquid paraffin oils, isoparaffin oils and synthetic hydrocarbons as well as di-n-alkyl ethers containing a total of 12 to 36 carbon atoms, particularly 12 to 24 carbon atoms such as, for example, di-n-octyl ether, di-n-decyl ether, di-n-nonyl ether, di-n-undecyl ether, di-n-dodecyl ether, n-hexyl n-octyl ether, n-octyl n-decyl ether, n-decyl n-undecyl ether, n-undecyl n-dodecyl ether and n-hexyl n-undecyl ether and di-tert.butyl ether, diisopentyl ether, di-3-ethyldecyl ether, tert.butyl n-octyl ether, isopentyl n-octyl ether and 2-methylpentyl n-octyl ether. The commercial products 1,3-di-(2-ethylhexyl)cyclohexane (Cetiol® S) and di-n-octyl ether (Cetiol® OE) can be preferred.

Ester oils. Ester oils refer to the esters of $C_6$-$C_{30}$ fatty acids with $C_2$-$C_{30}$ fatty alcohols. Monoesters of fatty acids with alcohols having 2 to 24 carbon atoms are preferred. Examples of fatty acids moieties utilized in the esters are caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachidonic acid, gadoleic acid, behenic acid and erucic acid as well as their industrial mixtures, that e.g. result from cracking of natural fats and oils, from the oxidation of aldehydes from Roelen's Oxo Synthesis or from the dimerization of unsaturated fatty acids. Examples for the fatty alcohol moieties in the ester oils are isopropyl alcohol, caproyl alcohol, capryl alcohol, 2-ethylhexyl alcohol, 1-decanol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol as well as their technical mixtures, that e.g. result from the high pressure hydrogenation of industrial methyl esters based on fats and oils or aldehydes from Roelen's oxo synthesis as well as the monomer fraction on the dimerization of unsaturated fatty alcohols. According to the invention, isopropyl myristate (Rilanit® IPM), isononanoic acid C16-18 alkyl ester (Cetiol® SN), 2-ethylhexyl palmitate (Cegesoft® 24), Stearic acid 2-ethylhexyl ester (Cetiol® 868), Cetyl oleate, glycerine tricaprylate, cocofatty alcohol caprinate/-caprylate (Cetiol® LC), n-butyl stearate, oleyl erucate (Cetiol® J 600), isopropyl palmitate (Rilanit® IPP), oleyl oleate (Cetiol®), lauric acid hexyl ester (Cetiol® A), di-n-butyl adipate (Cetiol® B), myristyl myristate (Cetiol® MM), cetearyl isononanoate (Cetiol® SN), oleic acid decyl ester (Cetiol® V) are particularly preferred.

Dicarboxylic acid esters such as di-n-butyl adipate, di-(2-ethylhexyl) adipate, di-(2-ethylhexyl) succinate and di-isotridecyl acetate as well as diol esters such as ethylene glycol dioleate, ethylene glycol di-isotridecanoate, propylene glycol di(2-ethylhexanoate), propylene glycol di-isostearate, propylene glycol di-pelargonate, butanediol di-isostearate, neopentyl glycol dicaprylate, symmetrical, unsymmetrical or cyclic esters of carbon dioxide with fatty alcohols, e.g. as described in DE-OS 197 56 454, glycerine carbonate or dicaprylyl carbonate (Cetiol® CC), trifatty acid esters of saturated and/or unsaturated linear and/or branched fatty acids with glycerine, fatty acid partial glycerides, under which are understood monoglycerides, diglycerides and their industrial mixtures. When using industrial products, minor amounts of triglycerides may still be contained as a result of the production process. The partial glycerides preferably comply with Formula (D4-I)—

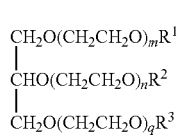

(D4-I)

wherein $R^1$, $R^2$ and $R^3$ are each independently hydrogen or a linear or branched, saturated and/or unsaturated acyl group containing 6 to 22 carbon atoms, preferably 12 to 18 carbon atoms, with the proviso that at least one of these groups is an acyl group and at least one of these groups is hydrogen. The sum of (m+n+q) is 0 or numbers from 1 to 100, preferably 0 or 5 to 25. Preferably, $R^1$ is an acyl group and $R^2$ and $R^3$ are hydrogen, and the sum of (m+n+q) is 0. Typical examples are mono- and/or diglycerides based on caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachidonic acid, gadoleic acid, behenic acid and erucic acid as well as their industrial mixtures. Oleic acid monoglycerides are preferably employed.

The amount of natural and synthetic cosmetic oil bodies added to compositions according to the invention is usually 0.1 to 30 wt. %, based on the total end-use preparation, preferably 0.1 to 20 wt. % and particularly 0.1 to 15 wt. %.

Moreover, the composition can comprise an enzyme as a conditioner. According to the invention, particularly preferred enzymes are selected from a group made up of proteases, lipases, transglutaminases, oxidases and peroxidases.

Although each of the cited conditioners alone already provides a satisfactory result, in the context of the present invention all embodiments are also included, in which the composition comprises a plurality of conditioners even from different groups.

By the addition of a UV filter, both the composition itself as well as the treated keratinic fibers can be protected against damage from UV radiation. Consequently, at least one UV filter is preferably added to the composition. The suitable UV filters are not generally limited in regard to their structure and their physical properties. Indeed, all UV filters that can be employed in the cosmetic field having an absorption maximum in the UVA (315-400 nm), in the UVB (280-315 nm) or in the UVC (<280 nm) regions are suitable. UV filters having an absorption maximum in the UVB region, especially in the range from about 280 to about 300 nm, are particularly preferred.

Inventively preferred UV-filters are chosen from substituted benzophenones, p-aminobenzoates, diphenylacrylates, cinnamates, salicylates, benzimidazoles and o-aminobenzoates.

The composition preferably comprises UV filters in quantities of 0.01 to 5 wt. %, based on the total end-use preparation. Quantities of 0.1-2.5 wt. % are preferred.

Depending on the type of the agent according to the invention, it may be necessary for them to additionally include at least one surfactant. This is particularly true for styling foams, to which are generally added certain surfactants as foam forming and/or foam-stabilizing ingredients.

For example, cationic surfactants can be added, as have already been described above as suitable conditioners. The above descriptions are also valid in regard to the preferred cationic surfactants and the added quantities.

In addition to or instead of the cationic surfactants, the agents can comprise further surfactants or emulsifiers, wherein in principle both anionic as well as ampholytic and non-ionic surfactants and all types of known emulsifiers are suitable. The group of the ampholytic or also amphoteric surfactants includes zwitterionic surfactants and ampholytes. The surfactants can already have an emulsifying action.

Suitable anionic surfactants are in principle all anionic surface-active materials that are suitable for use on the human body. They are characterized by a water solubilizing anionic group, such as e.g. a carboxylate, sulfate, sulfonate or phosphate group and a lipophilic alkyl group containing about 8 to 30 carbon atoms. In addition, the molecule may comprise glycol or polyglycol ether groups, ester, ether and amide groups as well as hydroxyl groups. Exemplary suitable anionic surfactants are, each in the form of the sodium, potassium and ammonium as well as the mono, di and trialkanolammonium salts containing 2 to 4 carbon atoms in the alkanol group— linear and branched fatty acids with 8 to 30 carbon atoms (soaps), ether carboxylic acids of the formula R—O—($CH_2$—$CH_2O$)$_x$—$CH_2$—COOH, in which R is a linear alkyl group containing 8 to 30 carbon atoms and x=0 or 1 to 16, acyl sarcosides with 8 to 24 carbon atoms in the acyl group, acyl taurides with 8 to 24 carbon atoms in the acyl group, acyl isethionates with 8 to 24 carbon atoms in the acyl group, mono- and dialkyl esters of sulfosuccinic acid with 8 to 24 carbon atoms in the alkyl group and mono-alkyl polyoxyethyl esters of sulfosuccinic acid with 8 to 24 carbon atoms in the alkyl group and 1 to 6 oxyethylene groups, linear alkane sulfonates containing 8 to 24 carbon atoms, linear alpha-olefin sulfonates containing 8 to 24 carbon atoms, alpha-sulfo fatty acid methyl esters of fatty acids containing 8 to 30 carbon atoms, alkyl sulfates and alkyl polyglycol ether sulfates of formula R—O($CH_2$—$CH_2O$)$_x$—$SO_3H$, in which R is preferably a linear alkyl group containing 8 to 30 carbon atoms and x=0 or 1 to 12, mixtures of surface-active hydroxysulfonates, sulfated hydroxyalkyl polyethylene glycol ethers and/or hydroxyalkylene propylene glycol ethers, sulfonated unsaturated fatty acids with 8 to 24 carbon atoms and 1 to 6 double bonds, esters of tartaric acid and citric acid with alcohols, which represent the addition products of about 2-15 molecules of ethylene oxide and/or propylene oxide on fatty alcohols containing 8 to 22 carbon atoms, alkyl- and/or alkenyl ether phosphates of Formula (E1-I)

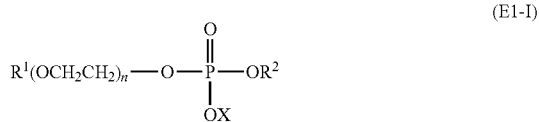

wherein $R^1$ preferably is an aliphatic hydrocarbon group containing 8 to 30 carbon atoms, $R^2$ is hydrogen, a $(CH_2CH_2O)_n R^1$ group or X, n is a number from 1 to 10, and X is hydrogen, an alkali- or alkaline earth metal or $NR^3R^4R^5R^6$, with $R^3$ to $R^6$, independently of each other standing for a C1 to C4 hydrocarbon group, sulfated fatty acid alkylene glycol esters of Formula (E1-II)

wherein $R^7CO-$ is a linear or branched, aliphatic, saturated and/or unsaturated acyl group containing 6 to 22 carbon atoms, Alk is $CH_2CH_2$, $CHCH_3CH_2$ and/or $CH_2CHCH_3$, n is a number from 0.5 to 5 and M is a cation, such as those described in DE-OS 197 36 906, monoglyceride sulfates and monoglyceride ether sulfates of Formula (E1-III)

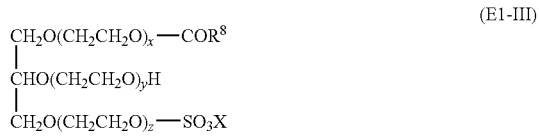

wherein $R^8CO$ is a linear or branched acyl group containing 6 to 22 carbon atoms, the sum of x, y and z is 0 or is a number from 1 to 30, preferably 2 to 10, and X is an alkali metal or alkaline earth metal. In the context of the invention, typical examples of suitable monoglyceride (ether) sulfates are the reaction products of lauric acid monoglyceride, cocoa fatty acid monoglyceride, palmitic acid monoglyceride, stearic acid monoglyceride, oleic acid monoglyceride and tallow fatty acid monoglyceride as well as their ethylene oxide adducts with sulfur trioxide or chlorosulfonic acid in the form of their sodium salts. Preferably, monoglyceride sulfates of Formula (E1-III) are added, in which $R^8CO$ is a linear acyl group containing 8 to 18 carbon atoms, amido ether carboxylic acids, amido ether carboxylic acids, condensation products of $C_8$-$C_{30}$ fatty alcohols with protein hydrolyzates and/or amino acids and their derivatives, which are known to the person skilled in the art as albumin fatty acid condensates, such as the Lamepon® types, Gluadin® types, Hostapon® KCG or the Amisoft® types.

Preferred anionic surfactants include alkyl sulfates, alkyl polyglycol ether sulfates and ether carboxylic acids with 10 to 18 C atoms in the alkyl group and up to 12 glycol ether groups in the molecule, sulfosuccinic acid mono and dialkyl esters with 8 to 18 C atoms in the alkyl group and sulfosuccinic acid mono-alkyl polyoxyethyl esters with 8 to 18 C atoms in the alkyl group and 1 to 6 oxyethylene groups, monoglycerine disulfates, alkyl- and alkenyl ether phosphates as well as albumin fatty acid condensates.

Zwitterionic surfactants are designated as those surface-active compounds that carry at least one quaternary ammonium group and at least one $-COO^{(-)}$ or $SO_3^{(-)}$ group in the molecule. Particularly suitable zwitterionic surfactants are the so-called betaines such as the N-alkyl-N,N-dimethylammonium glycinates, for example the cocoalkyl dimethylammonium glycinate, N-acylaminopropyl-N,N-dimethylammonium glycinates, for example the cocoacylaminopropyl dimethylammonium glycinate, and 2-alkyl-3-carboxymethyl-3-hydroxyethyl imidazolines with 8 to 18 carbon atoms in each of the alkyl or acyl groups, as well as cocoacylaminoethyl hydroxyethyl carboxymethyl glycinate. A preferred zwitterionic surfactant is the fatty acid amide derivative, known under the INCI name Cocamidopropyl Betaine.

Ampholytes are understood to include such surface-active compounds that apart from a $C_{8-24}$ alkyl or acyl group, comprise at least one free amino group and at least one $-COOH$ or $-SO_3H$ group in the molecule, and are able to form internal salts. Examples of suitable ampholytes are N-alkylglycines, N-alkyl propionic acids, N-alkylamino butyric acids, N-alkylimino dipropionic acids, N-hydroxyethyl-N-alkylamidopropylglycine, N-alkyltaurines, N-alkylsarcosines, 2-alkylamino propionic acids and alkylamino acetic acids, each with about 8 to 24 carbon atoms in the alkyl group. Particularly preferred ampholytes are N-cocoalkylamino propionate, cocoacylaminoethylamino propionate and $C_{12}$-$C_{18}$ acyl sarcosine.

Non-ionic surfactants comprise e.g. a polyol group, a polyalkylene glycol ether group or a combination of polyol ether groups and polyglycol ether groups as the hydrophilic group. Exemplary compounds of this type include— addition products of 2 to 50 moles ethylene oxide and/or 1 to 5 moles propylene oxide to linear and branched fatty alcohols containing 8 to 30 carbon atoms, to fatty acids containing 8 to 30 carbon atoms and to alkyl phenols containing 8 to 15 carbon atoms in the alkyl group, methyl or $C_2$-$C_6$ alkyl group end blocked addition products of 2 to 50 moles ethylene oxide and/or 1 to 5 moles propylene oxide to linear and branched fatty alcohols with 8 to 30 carbon atoms, to fatty acids with 8 to 30 carbon atoms and to alkyl phenols with 8 to 15 carbon atoms in the alkyl group, such as, for example, the commercially available types Dehydrol® LS, Dehydrol® LT (Cognis), $C_{12}$-$C_{30}$ fatty acid mono- and diesters of addition products of 1 to 30 moles ethylene oxide to glycerine, addition products of 5 to 60 moles ethylene oxide on castor oil and hydrogenated castor oil, polyol esters of fatty acids, such as, for example, the commercial product Hydagen® HSP (Cognis) or Sovermol types (Cognis), alkoxylated triglycerides, alkoxylated fatty acid alkyl esters according to Formula (E4-I)—

amine oxides, hydroxy mixed ethers, sorbitol esters of fatty acids and addition products of ethylene oxide to sorbitol esters of fatty acids such as e.g. the polysorbates, sugar esters of fatty acids and addition products of ethylene oxide to sugar esters of fatty acids, addition products of ethylene oxide to fatty acid alkanolamides and fatty amines, alkyl and alkenyl oligoglycosides sugar surfactants according to Formula (E4-II)—

$$R^4O\text{-}[G]_p \qquad (E4\text{-}II)$$

wherein $R^4$ is an alkyl or alkenyl group containing 4 to 22 carbon atoms, G is a sugar group containing 5 or 6 carbon atoms, and p is a number from 1 to 10. They can be obtained according to the appropriate methods of preparative organic chemistry.

Preferred alkyl and/or alkenyl oligoglycosides are accordingly alkyl and/or alkenyl oligoglucosides The index value p in the general Formula (E4-II) represents the degree of oligomerization (DP), i.e. the distribution of mono and oligoglycosides, and stands for a number between 1 and 10. Whereas in a given compound, p must always be a whole number and here above all can assume the values p=1 to 6, the value p for a specific alkyl oligoglycoside is an analytically determined calculated quantity that mostly represents a fractional number. Preferably, alkyl and/or alkenyl oligoglycosides are employed with an average degree of oligomerization p of 1.1 to 3.0. Alkyl oligoglucosides based on hydrogenated $C_{12/14}$ coco alcohol with a DP of 1 to 3 are preferred Alkylene oxide addition products to saturated, linear fatty alcohols and fatty acids, each with 2 to 30 moles ethylene oxide per mole fatty alcohol or fatty acid, have proved to be preferred non-ionic surfactants. Preparations with excellent properties are also obtained when they comprise fatty acid esters of ethoxylated glycerin as the non-ionic surfactant.

These compounds are characterized by the following parameters. The alkyl group R comprises 6 to 22 carbon atoms and may be both linear and also branched. Primary linear aliphatic groups and aliphatic groups that are methyl-branched in the 2-position, are preferred. Such alkyl groups are for example 1-octyl, 1-decyl, 1-lauryl, 1-myristyl, 1-cetyl and 1-stearyl. 1-Octyl, 1-decyl, 1-lauryl, 1-myristyl are particularly preferred. On using so-called "oxo alcohols" as starting materials, compounds with an odd number of carbon atoms in the alkyl chain preponderate.

Sugar surfactants can also be included as the non-ionic surfactants. They are preferably present in amounts of 0.1 to 20 wt. %, based on the total composition. Quantities of 0.5 to 15 wt. % are particularly preferred and quantities of 0.5 to 7.5 wt. % are quite particularly preferred.

For compounds with alkyl groups that are used as surfactants, they may each be pure substances. However, it is normally preferred to start with natural vegetal or animal raw materials for the manufacture of these materials, with the result that mixtures of substances are obtained, which have different alkyl chain lengths that depend on each raw material.

For surfactants, which are represented by the addition products of ethylene oxide and/or propylene oxide to fatty alcohols or derivatives of these addition products, both products with a "normal" homolog distribution as well as those with a narrow homolog distribution may be used. The term "normal" homolog distribution is understood to mean mixtures of homologs obtained from the reaction of fatty alcohols and alkylene oxide using alkali metals, alkali metal hydroxides or alkali metal alcoholates as catalysts. On the other hand, narrow homolog distributions are obtained if e.g. hydrotalcite, alkaline earth metal salts of ether carboxylic acids, alkaline earth metal oxides, hydroxides or alcoholates are used as catalysts. The use of products with a narrow homolog distribution can be preferred.

Additional surfactants are generally added in quantities of 0.1-45 wt. %, preferably 0.5-30 wt. % and quite particularly preferably from 0.5-25 wt. %, based on the total composition. The added quantity depends on the purpose of the inventive agent. For a shampoo or other cleansing agent, surfactant levels above 45 wt. % can be typical.

The compositions can additionally comprise at least one emulsifier. Emulsifiers act at the interface to produce water or oil-stable adsorption layers that protect the dispersed droplets against coalescence and thereby stabilize the emulsion. Thus, emulsifiers, like surfactants are composed of hydrophobic and hydrophilic molecular moieties. Hydrophilic emulsifiers preferably form O/W emulsions and hydrophobic emulsifiers preferably form W/O emulsions. The choice of this emulsifying surfactant or emulsifier depends on the materials being dispersed and the respective external phase as well as the fineness of the emulsion. Exemplary emulsifiers usable according to the invention include—

- Addition products of 4 to 100 moles ethylene oxide and/or 1 to 5 moles propylene oxide to linear fatty alcohols containing 8 to 22 carbon atoms, to fatty acids containing 12 to 22 carbon atoms and to alkyl phenols containing 8 to 15 carbon atoms in the alkyl group,
- $C_{12}$-$C_{22}$ fatty acid mono- and diesters of addition products of 1 to 30 moles ethylene oxide on polyols containing 3 to 6 carbon atoms, especially glycerine,
- ethylene oxide and polyglycerine addition products on methyl glucoside fatty acid esters, fatty acid alkanolamides and fatty acid glucamides,
- $C_8$-$C_{22}$ alkyl mono and oligoglycosides and their ethoxylated analogs, wherein the degrees of oligomerization are 1.1 to 5, particularly 1.2 to 2.0 and glucose as the sugar component are preferred,
- mixtures of alkyl (oligo) glucosides and fatty alcohols, for example the commercially available product Montanov® 68,
- addition products of 5 to 60 moles ethylene oxide on castor oil and hydrogenated castor oil,
- partial esters of polyols containing 3-6 carbon atoms with saturated fatty acids containing 8 to 22 carbon atoms,
- sterols. Sterols are understood to mean a group of steroids, which carry a hydroxyl group on carbon atom 3 of the steroid skeleton and are isolated from both animal tissue (zoosterols) and vegetal fats (phytosterols). Examples of zoosterols are cholesterol and lanosterol. Examples of suitable phytosterols are ergosterol, stigmasterol and sitosterol. Sterols, the so-called mycosterols, are also isolated from fungi and yeasts.
- phospholipids. Among these are principally meant the glucose-phospholipids, which are obtained e.g. as lecithins or phosphatidyl cholines from e.g. egg yolk or plant seeds (e.g. soya beans).
- fatty acid esters of sugars and sugar alcohols such as sorbitol,
- polyglycerines and polyglycerine derivatives such as for example polyglycerine poly-12-hydroxystearate (commercial product Dehymuls® PGPH),
- linear and branched fatty acids containing 8 to 30 carbon atoms and their Na, K, ammonium, Ca, Mg and Zn salts.

Emulsifiers are preferably added in amounts of 0.1 to 25 wt. %, especially 0.1 to 3 wt. %, based on the total composition.

Non-ionic emulsifiers with an HLB value of 8 to 18 are preferred. Non-ionic emulsifiers with an HLB value of 10 to 16 are particularly preferred according to the invention.

The inventive compositions can further comprise at least one substantive dye. The fibers treated with compositions of this type can be shaped and dyed in one step.

Substantive dyes are usually nitrophenylenediamines, nitroamino phenols, azo dyes, anthraquinones or indophenols. Preferred substantive dyestuffs are the compounds known under the international designations or trade names HC Yellow 2, HC Yellow 4, HC Yellow 5, HC Yellow 6, HC Yellow12, Acid Yellow 1, Acid Yellow 10, Acid Yellow 23, Acid Yellow 36, HC Orange 1, Disperse Orange 3, Acid Orange 7, HC Red 1, HC Red 3, HC Red 10, HC Red 11, HC Red 13, Acid Red 33, Acid Red 52, HC Red BN, Pigment Red 57:1, HC Blue 2, HC Blue 11, HC Blue 12, Disperse Blue 3, Acid Blue 7, Acid Green 50, HC Violet 1, Disperse Violet 1, Disperse Violet 4, Acid Violet 43, Disperse Black 9, Acid Black 1, and Acid Black 52 known compounds as well as 1,4-diamino-2-nitrobenzene, 2-amino-4-nitrophenol, 1,4-bis(β-hydroxyethyl)amino-2-nitrobenzene, 3-nitro-4(β-hydroxyethyl)aminophenol, 2-(2'-hydroxyethyl)amino-4-6-dinitrophenol, 1-(2'-hydroxyethyl)amino-4-methyl-2-nitrobenzene, 1-amino-4-(2'-hydroxyethyl)-amino-5-chloro-2-nitrobenzene, 4-amino-3-nitrophenol, 1-(2'-ureidoethyl)amino-4-nitrobenzene, 4-amino-2-nitrodiphenylamine-2'-carboxylic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid and 2-chloro-6-ethylamino-1-hydroxy-4-nitrobenzene.

Cationic substantive dyes are preferably employed. Particular preference is given here to
a) cationic triphenylmethane dyes such as Basic Blue 7, Basic Blue 26, Basic Violet 2 and Basic Violet 14,
b) aromatic systems which are substituted by a quaternary nitrogen group, such as Basic Yellow 57, Basic Red 76, Basic Blue 99, Basic Brown 16 and Basic Brown 17, and
c) substantive dyes, which comprise a heterocycle that has at least one quaternary nitrogen atom, as specified, for example, in EP-A2-998 908 in claims 6 to 11, which is explicitly incorporated herein by reference.

Inventive compositions according to this embodiment comprise the substantive dyes preferably in a quantity of 0.001 to 20 wt. %, based on the total composition.

In addition, the compositions according to the invention can also comprise naturally occurring dyestuffs as are contained for example in henna red, henna neutral, henna black, camomile leaves, sandalwood, black tea, alder buckthorn bark, sage, logwood, madder root, cachou, cedar and alkanet root.

It is not required that each substantive dyestuff be pure compounds. In fact, the compositions according to the invention, due to the manufacturing processes for the individual dyestuffs, may comprise minor quantities of even more components, in so far as the latter have no detrimental influence on the styling result or that they must be excluded on other grounds, e.g. toxicological.

In addition to the cited components, the compositions can furthermore comprise all active substances, additives and auxiliaries known for such cosmetics.

Further exemplary active products, auxiliaries and additives include—
thickeners like agar-agar, guar gum, alginates, xanthane gum, gum arabica, karaya gum, locust bean flour, linseed gums, dextrans, cellulose derivatives, e.g. methyl cellulose, hydroxyalkyl cellulose and carboxymethyl cellulose, starch fractions and derivatives such as amylose, amylopectin and dextrins, clays such as e.g. bentonite or synthetic hydrocolloids such as e.g. polyvinyl alcohol, and optionally crosslinked polyacrylates,
structurants such as maleic acid and lactic acid,
perfume oils, dimethyl isosorbitol and cyclodextrins,
solvents and solubilizers such as ethanol, isopropanol, ethylene glycol, propylene glycol, glycerine and diethylene glycol,
quaternized amines, such as methyl 1-alkylamidoethyl-2-alkylimidazolium methosulfate
defoamers such as silicones,
dyestuffs to color the composition,
anti-dandruff active materials such as Piroctone Olamine, zinc Omadine and Climbazole,
substances for adjusting the pH, such as, for example, customary acids, in particular food acids, and bases,
cholesterol,
texturizers such as sugar esters, polyol esters or polyol alkyl ethers,
fats and waxes such as spermaceti, beeswax, montan wax and paraffins,
fatty acid alkanolamides,
chelating agents such as EDTA, NTA, β-alanine diacetic acid and phosphonic acids,
swelling and penetration compositions such as glycerine, propylene glycol monoethyl ether, carbonates, hydrogen carbonates, guanidines, ureas, and primary, secondary and tertiary phosphates,
opacifiers such as latex, styrene/PVP copolymers and styrene/acrylamide copolymers,
pearlizing compositions such as ethylene glycol mono- and distearate as well as PEG-3-distearate,
preservatives,
stabilizers for hydrogen peroxide and other oxidizing compositions,
propellants such as propane-butane mixtures, $N_2O$, dimethyl ether, $CO_2$ and air, and
antioxidants.

Regarding further optional ingredients and their amounts used, reference is expressly made to the relevant handbooks known to the person skilled in the art.

The formulation of the inventive agents can be in all usual cosmetic forms, for example, in the form of solutions that can be applied as facial or hair water or pump or aerosol spray onto the skin or hair to be treated, in the form of creams, emulsions, waxes, gels or also surfactant-containing foaming solutions or other preparations, which are suitable for application on the skin or the hair.

However, the inventive compositions for the temporary treatment of keratinic fibers preferably concern styling gels, pump hair sprays, aerosol hair sprays, pump hair foams and aerosol hair foams.

Hair foams are understood in this regard to mean compositions that form a foam when removed from a suitable container. It may be required to add ingredients to the agent which promote foaming or which stabilize an initially formed foam. Surfactants and/or emulsifiers are particularly suitable for this, as has been described previously. Preferably, surfactants from the group of the cationic surfactants are utilized.

Hair creams and hair gels generally comprise structurants and/or thickening polymers, which lend the desired consistency to the products. They are typically used in amounts of 0.1 to 10 wt. %, based on the total composition. Quantities of 0.5 to 5 wt. %, particularly 0.5 to 3 wt. %, are preferred.

When the inventive agents concern an aerosol product then this imperatively comprises a propellant.

Inventively suitable exemplary propellants are $N_2O$, dimethyl ether, $CO_2$, air and alkynes containing 3 to 5 carbon atoms, such as propane, n-butane, iso-butane, n-pentane and iso-pentane, and their mixtures. Dimethyl ether, propane, n-butane, iso-butane and their mixtures are preferred.

The cited alkanes, mixtures of the cited alkanes or mixtures of the cited alkanes with dimethyl ether are preferred as the sole propellant. However, the invention also explicitly includes the joint utilization with propellants of the fluorochlorohydrocarbon type, but especially fluorinated hydrocarbons.

In regard to the weight ratio of propellant to the usual ingredients of the preparation, the size of the aerosol droplets or the foam bubbles and the relevant size distribution can be adjusted for a given spray device.

The quantity of added propellant varies as a function of the actual composition of the agent, the packaging used and the desired product type, for example hair spray or hair foam. When a conventional spray device is used, aerosol foam products preferably comprise the propellant in amounts of 1 to 35 wt. %, based on the total composition. Quantities of 2 to 30 wt. %, especially 3 to 15 wt %, are particularly preferred. Aerosol sprays generally comprise greater amounts of propellant. In this case the propellant is preferably added in amounts of 30 to 98 wt. %, based on the total composition. Quantities of 40 to 95 wt. %, especially 50 to 95 wt. %, are particularly preferred.

The aerosol products can be manufactured according to conventional techniques. Generally, all ingredients of the agent, excepting the propellant, are charged into a suitable pressure-resistant container. This is thereupon sealed with a valve. The desired quantity of propellant is then filled by means of conventional techniques.

A second subject matter of the invention is the use of inventive compositions (especially compositions of the claims 1 to 14) for the temporary shaping of keratinic fibers.

The invention additionally relates to methods for the temporary shaping of hair by using the inventive compositions (especially compositions of the claims 1 to 14).

According to a first embodiment, the hair is brought into the desired shape and the resulting hairstyle is fixed with an inventive composition. This procedure is available if the agent is in the form of a pump or aerosol hair spray.

According to a second embodiment, an inventive composition is applied onto the hair before/and or during the shaping procedure and the hair is brought into the desired shape in the presence of the composition. In particular, this procedure is available if the agent is in the form of a styling gel, a styling cream or a pump or aerosol hair foam. In a further step the shaped hairstyle can optionally be fixed once more with an inventive composition that is in particular in the form of a pump or aerosol hair spray.

I claim:

1. Cosmetic composition for the temporary styling of keratinic fibers comprising a polysilicic acid in a cosmetically acceptable carrier, wherein the polysilicic acid is coated with at least one copolymer A, wherein copolymer A is formed from at least one monomer A1 according to Formula A1—

$$H_2C=C(R^1)-C(=O)-N(H)-(CH_2)_n-\text{Ar}(R^3)(OH)(R^2) \tag{A1}$$

wherein
$R^1$ is H or $CH_3$,
$R^2$ and $R^3$ are each independently H, OH, $C_{1-10}$ alkyl or $C_{1-10}$ alkoxy, with the proviso that at least one of $R^2$ or $R^3$ is OH, and
n is a whole number from 0 to 20; and at least one monomer A2 according to Formula A2—

$$H_2C=C(R^4)-C(=O)-Z-R^5 \tag{A2}$$

wherein
$R^4$ is H or $CH_3$,
Z is O or NH, and
$R^5$ is $C_{1-30}$ alkyl or a $C_{1-30}$ alkylene $C_{1-30}$ alkyl ether group wherein copolymer A is formed from 5 to 25 wt. % monomer A1 and 95 to 75 wt. % monomer A2.

2. Cosmetic composition according to claim 1, wherein $R^1$ in Formula A1 is $CH_3$.

3. Cosmetic composition according to claim 1, wherein $R^2$ and $R^3$ in Formula 1 are each independently H, OH, methyl, ethyl, n-propyl, iso-propyl, n-butyl, iso-butyl, tert.-butyl or n-pentyl, with the proviso that at least one of $R^2$ or $R^3$ is OH.

4. Cosmetic composition according to claim 1, wherein n in Formula A1 is a whole number from 1 to 10.

5. Cosmetic composition according to claim 1, wherein $R^4$ in Formula A2 is H.

6. Cosmetic composition according to claim 1, wherein Z in Formula A2 is O.

7. Cosmetic composition according to claim 1, wherein $R^5$ in Formula A2 is methyl, ethyl, n-propyl, iso-propyl, n-butyl, iso-butyl, tert.-butyl, n-pentyl, methyleneoxy methyl, methyleneoxy ethyl, methyleneoxy n-propyl, methyleneoxy iso-propyl, methyleneoxy n-butyl, methyleneoxy iso-butyl, methyleneoxy tert.-butyl, methyleneoxy n-pentyl, ethyleneoxy methyl, ethyleneoxy ethyl, ethyleneoxy n-propyl, ethyleneoxy iso-propyl, ethyleneoxy n-butyl, ethyleneoxy iso-butyl, ethyleneoxy tert.-butyl, ethyleneoxy n-pentyl, n-propyleneoxy methyl, n-propyleneoxy ethyl, n-propyleneoxy n-propyl, n-propyleneoxy iso-propyl, n-propyleneoxy n-butyl, n-propyleneoxy iso-butyl, n-propyleneoxy tert.-butyl or n-propyleneoxy n-pentyl.

8. Cosmetic composition according to claim 1, wherein, in monomer A1—
$R^1$ is $CH_3$,
$R^2$ and $R^3$ are each independently H or OH, with the proviso that only one of $R^2$ or $R^3$ is OH, and
n is 2; and
in monomer A2—
$R^4$ is H,
Z is O, and
$R^5$ is —$CH_2$—$CH_2$—O—$CH_3$.

9. Cosmetic composition according to claim 1, wherein the polysilicic acid is pyrogenic silica or precipitated silica.

10. Cosmetic composition according to claim 9, wherein the polysilicic acid is pyrogenic silica having a specific BET surface area of 25 to 600 $m^2/g$.

11. Cosmetic composition according to claim 9, wherein the polysilicic acid is pyrogenic silica having a primary particle size of 5 to 500 nm and an agglomerate size of 2 to 15 μm as measured by scanning electron microscopy.

12. Cosmetic composition according to claim 11, wherein the polysilicic acid is precipitated silica having a specific BET surface area of 30 to 800 $m^2/g$.

13. Cosmetic composition according to claim 9, wherein the polysilicic acid is precipitated silica having a primary particle size of 5 to 200 nm and an agglomerate size of 1 to 40 μm as measured by scanning electron microscopy.

14. Cosmetic composition according to claim 1, wherein the copolymer A-coated polysilicic acid is present in an amount of 0.001 to 40 wt. %, based on total weight of the composition.

* * * * *